(12) United States Patent
Albert

(10) Patent No.: US 6,362,176 B1
(45) Date of Patent: Mar. 26, 2002

(54) COMPOSITIONS, METHODS AND KITS FOR TREATING RHEUMATOID ARTHRITIS

(75) Inventor: Daniel A. Albert, Philadelphia, PA (US)

(73) Assignee: Super Gen, Inc., Dublin, CA (US)

( * ) Notice: Subject to any disclaimer, the term of this patent is extended or adjusted under 35 U.S.C. 154(b) by 0 days.

(21) Appl. No.: 09/620,166

(22) Filed: Jul. 20, 2000

Related U.S. Application Data

(63) Continuation of application No. 09/092,286, filed on Jun. 5, 1998, now abandoned.

(51) Int. Cl.[7] ....................... A61K 31/55; A61K 31/495
(52) U.S. Cl. ........................... 514/211.15; 514/211.11; 514/252.02; 514/252.14
(58) Field of Search ....................... 514/211.02, 211.15, 514/252.02, 252.14

(56) References Cited

FOREIGN PATENT DOCUMENTS

| | | |
|---|---|---|
| DE | 196 36 252 | 3/1998 |
| WO | WO 96/35419 | 11/1996 |

OTHER PUBLICATIONS

Albert, D. et al., "Deoxycoformycin (Pentostatin) for the Treatment of Rheumatoid Arthritis" (Abstract), American College of Rheumatology, Oct. 1995.

Cronstein, B., "The Antirheumatic Agents Sulphasalazine and Methotrexate Share an Anti–Inflammatory Mechanism", British Journal of Rheumatology, vol. 34, Suppl. 2, 1995, pp. 30–32.

Ho, A. et al., "Induction of Intracellular and Plasma 2',5'–Oligoadenylate Synthetase by Pentostatin", Leukemia, vol. 6, No. 3, Mar. 1992, pp. 209–214.

Ho, A. et al., "Long–Term Effects of 2'–Deoxycoformycin Treatment on Cytokine Production in Patients with Hairy Cell Leukemia", Leukemia, vol. 4, No. 8, Aug. 1990, pp. 584–589.

Ho, A. et al., "Clinical Response to Deoxycoformycin in Chronic Lymphoid Neoplasms and Biochemical Changes in Circulating Malignant Cells In Vivo", Blood, vol. 72, No. 6, Dec. 1988, pp. 1894–1890.

Smyth, J. et al., "The Clinical Pharmacology of the Adenosine Deaminase Inhibitor 2'–Deoxycoformycin", Cancer Chemother. Pharmacol., vol. 5, 1980, pp. 93–101.

Physician's Desk Reference, Product Information, pp. 2733–2736 (1997).

Zvaifler, N., "Etiology and Pathogenesis of Rheumatoid Arthritis", Rheumatoid Arthritis, Lippincott (publ.) (1985) pp. 659–673.

Gilbertsen, R., "Effects of Pentostatin (2'Deoxycoformycin), An Inhibitor of Adenosine Deaminase, On Type II Collagen–Induced Arthritis in Rats", Journal of Immunopharmacology, vol. 7, No. 3, 1985, pp. 325–341.

"Primer on the Rheumatic Diseases" (8th Ed.), Gerald P. Rodnan et al. (Eds.), Arthritis Foundation, Atlanta, GA, (1983) pp. 83–95.

Carson, D. et al., "Differential Sensitivity of Human Leukemic T Cell Lines and B Cell Lines to Growth Inhibition by Deoxyadenosine", The Journal of Immunology, vol. 121, No. 5, Nov. 1978, pp. 1726–1731.

Hershfield, M., "Apparent Suicide Inactivation of Human Lymphoblast S–Adenosylhomocysteine hydrolase by 2'–Deoxyadenosine and Adenine Arabinoside", The Journal of Biological Chemistry, vol. 254, No. 1, Jan. 10, 1979, pp. 22–25.

Spiers, A. et al., "Remissions in Hairy–Cell Leukemia With Pentostatin (2'–Deoxycoformycin)", The New England Journal of Medicine, vol. 316, No. 14, Apr. 1987, pp. 825–830.

Tugwell, P. et al., "Combination Therapy with Cyclosporine and Methotrexate in Severe Rheumatoid Arthritis", The New England Journal of Medicine, vol. 333, No. 3, Jul. 1995, pp. 138–141.

Cohen, A. et al., "Deoxyadenosine triphosphate as a potentially toxic metabolite in adenosine deaminase deficiency", Proc. Natl. Acad. Sci. USA, vol. 75, No. 1, Jan. 1978, pp. 472–476.

Swanson, M. et al., "The Relation between Clinical Response and Immunologic Competence", The New England Journal of Medicine, vol. 277, No. 4, Jul. 1967, pp. 164–170.

Kotzin, B. et al., "Treatment of Intractable Rheumatoid Arthritis With Total Lymphoid Irradiation", The New England Journal of Medicine, vol. 305, No. 17, Oct. 1981, pp. 969–976.

Trentham, D. et al., "Clinical and Immunologic Effects of Fractionated Total Lymphoid Irradiation in Refractory Rheumatoid Arthritis", The New England Journal of Medicine, vol. 305, No. 17, Oct. 1981, pp. 976–982.

Wegelius, O. et al., "Fistula of the Thoracic Duct as Immunosuppressive Treatment in Rheumatoid Arthritis", Acta Med. Scand., vol. 187, 1970, pp. 539–544.

Seto, S. et al., "Mechanism of Deoxyadenosine and 2–Chlorodeoxyadenosine Toxicity to Nondividing Human Lymphocytes", J. Clin. Invest., vol. 75, Feb. 1985, pp. 377–383.

Cronstein, B., "Adenosine, an endogenous anti–inflammatory agent", Amer. Physiol. Soc., 1994, pp. 5–13.

Albert, D. et al., "Deoxyadenosine Toxicity and Cell Cycle Arrest in Hydroxyurea–Resistant S49 T–Lymphoma Cells", Experimental Cell Research, vol. 179, 1988, pp. 417–428.

(List continued on next page.)

*Primary Examiner*—Theodore J. Criares
(74) *Attorney, Agent, or Firm*—David J. Weitz; Wilson Sonsini Goodrich & Rosati

(57) ABSTRACT

Disclosed are methods of treating rheumatoid arthritis by coadministering synergistic effective amounts of pentostatin and methotrexate to a host in need thereof, and kits and compositions that include pentostatin and methotrexate.

23 Claims, No Drawings

OTHER PUBLICATIONS

Koller, C. et al., "Alterations in Erythrocyte Adenine Nucleotide Pools Resulting from 2'–Deoxycoformycin Therapy", Cancer Research, vol. 43, Mar. 1983, pp. 1409–1414.

Kurtzberg, J. et al., "Determinants of Deoxyadenosine Toxicity in Hybrids between Human T–and B—Lymphoblasts as a Model for the Development of Drug Resistance in T–Cell Acute Lymphoblastic Leukemia", Cancer Research, vol. 45, Apr. 1985, pp. 1579–1586.

Wortmann, R. et al., "Relationship of 5'–Nucleotidase Activity and Antileukemic Effect in 2'–Deoxycoformycin Therapy", Cancer Treatment Reports, vol. 66, No. 2, Feb. 1982, pp. 387–390.

Albert, D. et al., "The Mechanism of Inhibition and 'Reversal' of Mitogen–Induced Lymphocyte Activation in a Model of Adenosine Deaminase Deficiency", Cellular Immunology, vol. 86, 1984, pp. 510–517.

O'Brien, P., "Procedures for Comparing Samples with Multiple Endpoints", Biometrics, vol. 40, Dec. 1984, pp. 1079–1087.

Felson, D. et al., "The American College of Rheumatology Preliminary Core Set of Disease Activity Measures for Rheumatoid Arthritis Clinical Trials", Arthritis and Rheumatism, vol. 36, No. 6, Jun. 1993, pp. 729–740.

Johnston, J. et al., "The treatment of hairy–cell leukaemia with 2'–deoxycoformycin", British Journal of Haematology, vol. 63, 1986, pp. 525–534.

Major, P. et al., "Clinical Pharmacology of Deoxycoformycin", Blood, vol. 58, No. 1, Jul. 1981, pp. 91–96.

Mitchell, B. et al., "Purinogenic Immunodeficiency Diseases: Clinical Features and Molecular Mechanisms", Annals of Internal Medicine, vol. 92, 1980, pp. 826–831.

van Rijthoven, A. et al., "Cyclosporin treatment for rheumatoid arthritis: a placebo controlled, double blind, multicentre study", Annals of the Rheumatic Diseases, vol. 45, pp. 726–731. (1980).

Burmester, G. et al., "Ia+ T Cells In Synovial Fluid and Tissues of Patients with Rheumatoid Arthritis", Arthritis and Rheumatism, vol. 24, No. 11, Nov. 1981, pp. 1370–1376.

Agarwal, R. et al., "Tight–Binding Inhibitors–IV. Inhibition of Adenosine Deaminases by Various Inhibitors", Biochemical Pharmacology, vol. 26, 1977, pp. 359–367.

Lofter, W. et al. "2'–Deoxycoformycin Therapy in Adult T–Cell Leukemia/Lymphoma" Cancer, vol. 60, No. 11, 1987, pp. 2605–2608; Abstract.

McCowage G.B. et al., "Successful Treatment of Two Children With Langerhans' Cell Histiocytosis With 2' Deoxycoformycin" DIV. Pediatric Hematology/Oncology, vol. 18, No. 2, 1996; pp. 154–158.

COMPOSITIONS, METHODS AND KITS FOR TREATING RHEUMATOID ARTHRITIS

CROSS REFERENCE TO RELATED APPLICATION

This application is a continuation of U.S. application Ser. No. 09/092,286 filed Jun. 5, 1998, now abandoned.

BACKGROUND OF THE INVENTION

1. Field of the Invention

This invention relates to treatment of rheumatoid arthritis through coadministration of pentostatin and methotrexate and analogs and derivatives thereof.

2. Description of Related Art

Rheumatoid arthritis (RA) is a systematic inflammatory condition that results in swelling, pain, loss of motion, and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, thus including vessels, dendritic cells, T, B, and NK cells, macrophages, and clusters of plasma cells. Additionally, there is often a plethora of immunopathological mechanisms at work, including antigen-antibody complexes, polymorphonuclear neutrophils, inflammatory T cells, and activated macrophages. Eventually, these processes result in destruction of the integrity of the joint, resulting in deformity and permanent loss of function. A more detailed description of the etiology and physiology of RA can be found in Zvaifler, N., "Etiology and Pathogenesis of Rheumatoid Arthritis in Arthritis and Allied Conditions" 659–73 (ed. D. M. McCarty). This document, and all other documents or references, cited to herein are incorporated by reference as if reproduced completely herein.

Rheumatoid arthritis is a common disease affecting 1 to 2% of the world's population with a female to male predominance of 3–4:1. The peak incidence is in the third to fourth decade. Once acquired the disorder is chronic; therefore the prevalence of the disease increases as one examines increasing age groups. The disease is of unknown cause, although genetics may impact the risk of developing rheumatoid arthritis. Although it is not certain, some common infection or infections might trigger the autoimmune process in susceptible individuals. Environmental influences are not thought to play a major role in the development of the disease. Interestingly, exogenous estrogens in the form of BCPS appear to reduce the risk.

This disease is relentless and progressively destructive unless medical therapy is effective in reducing the degree of inflammation. While some individuals do well, most are significantly disabled by their disease and some are crippled. Surprisingly, the disease is responsible for a two-fold increased mortality and a 5-year reduction in the life expectancy of both males and females.

RA is classified as an autoimmune inflammatory disease. Autoimmune inflammatory diseases are conditions in which a body mounts an immune response to itself. Initiation of such diseases is not well understood, but involves both genetic predisposition and environmental factors. Such diseases are usually classified clinically in a variety of ways. For example, autoantibodies or self-reactive lymphocytes can be transferred to an otherwise healthy individual to see if the disease can be reproduced. Other ways to characterize autoimmune inflammatory diseases include establishment of animal models, family history, involvement of immune cells and antibodies, and responsiveness of the disease to immunosuppressive pharmaceuticals.

Autoimmune inflammatory diseases such as rheumatoid arthritis are difficult to treat primarily because their causative mechanisms are so difficult to understand. Autoimmune inflammatory diseases are multifactorial—a variety of events must occur before the disease symptoms become apparent. The interplay of these events is highly complex.

Accordingly, treatments for rheumatoid arthritis have been difficult to develop. Conventional therapeutic strategies have focused on monotherapies, i.e. administration of a single active compound to treat the disease. The most common monotherapies are based on a class of pharmaceuticals known as DMARDS—disease modifying anti-rheumatic drugs. These pharmaceuticals are generally administered over a period of time, and can, in some cases, provide temporary relief for patients suffering from RA.

Methotrexate is a common DMARD for rheumatoid arthritis. Approximately 70% of individuals with RA get some sort of favorable response, and over 50% are still on the drug five years after starting. Severity of disease does not determine the responsiveness of the patient although more severely affected individuals may have less complete responses. There is some controversy about how effective methotrexate is for the prevention of erosive and destructive changes as measured by radiographs, but it may ameliorate this aspect of the disease in addition to its effect on pain and improved function.

Once administered, the effects of methotrexate on articular swelling and tenderness may be seen as early as three to six weeks after administration. Methotrexate monotherapy has been shown, in limited circumstances, to maintain an initial clinical improvement for at least two years with continued therapy. Methotrexate is often administered parenterally with generally complete absorption. It is also known to be administered intramuscularly, with peak serum concentrations occurring in thirty to sixty minutes, or orally, in the form of tablets. When methotrexate monotherapy is discontinued, the RA usually worsens within three to six weeks.

However, a significant patient population is refractory to conventional DMARD monotherapy; they get only partial or no relief from administration of conventional DMARDS such as methotrexate. Additionally, many patients build up a tolerance to DMARDS, requiring increasingly stronger doses. This can create problems for such patients, because stronger doses can lead to increased incidences of undesirable side effects due to the DMARDS.

Recent studies of RA monotherapy illustrate these difficulties. For example, while about 70% of patients receiving methotrexate might be expected to obtain at least partial relief, less than 30% of the patients enter remission as defined by American College of Rheumatology (ACR) criteria. Up to 70% of the patients remain on methotrexate for two or more years.

The relative scarcity of effective therapies has motivated researchers to develop improved therapies. In one instance, researchers turned to 2'-deoxycoformycin, also referred to as pentostatin. A study done in England under Dr. Gabriel Panayi investigated pentostatin monotherapy. Dr. Panayi's group administered pentostatin to RA patients on a bi-weekly basis. Unfortunately, a significant flare (recurrence or exacerbation of disease symptoms) occurred in 9 of 11 patients at months 1 and 3 in terms of duration of morning stiffness and tender and swollen joints. The treatment was subsequently discontinued.

The inventor has noted similar but less dramatic results using pentostatin monotherapy on a monthly schedule. When the treatment was continued past the flare, approximately a third of the patients entered a pharmaceutical free remission for a period of weeks or months. However, this still does not represent a significant overall improvement from conventional DMARD therapy, and adds the concern of the flare to other treatment concerns. Consequently, the current pentostatin monotherapy regimen, while it does provide the clinician with another RA treatment option, does not represent a significant advance beyond current RA therapy.

There is therefore the need for improved compositions, methods and kits for treating rheumatoid arthritis beyond those currently available.

SUMMARY OF THE INVENTION

In one aspect, the invention relates to a method of treating rheumatoid arthritis comprising coadministering pentostatin and methotrexate to a host in need thereof. In another aspect, the invention relates to a composition comprising pentostatin and methotrexate. In yet another aspect, the invention relates to a kit comprising pentostatin and methotrexate.

DETAILED DESCRIPTION OF THE INVENTION

In one aspect, the invention relates to a method of treating rheumatoid arthritis comprising coadministering pentostatin and methotrexate to a host in need thereof. In another aspect, the invention relates to the method, wherein the pentostatin is coadministered intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically, or through local administration. In another aspect, the invention relates to the method, wherein the pentostatin is coadministered intraarticularly. In another aspect, the invention relates to the method, wherein the pentostatin is coadministered intravenously.

In still another aspect, the invention relates to the method wherein the pentostatin is coadministered in an amount up to about 4 mg/m$^2$ monthly. In yet another aspect, the invention relates to the method wherein the methotrexate is coadministered intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically or through local administration. In another aspect, the invention relates to the method wherein the methotrexate is coadministered orally.

In still another aspect, the invention relates to the method wherein the methotrexate is coadministered orally in the form of a tablet containing about 2.5 mg equivalent of methotrexate. In another aspect, the invention relates to the method wherein the methotrexate and pentostatin are coadministered coextensively. In yet another aspect, the invention relates to the method wherein the methotrexate and pentostatin are not coadministered coextensively.

In another aspect, the invention relates to the method wherein the methotrexate is coadministered over a period approximately coextensive with the pentostatin, but in a separate dosage form.

In yet another aspect, the invention relates to the method wherein the methotrexate is coadministered over an approximately coextensive period, but in a similar or the same dosage form, as the pentostatin.

In still another aspect, the invention relates to the method wherein both methotrexate and pentostatin are coadministered orally.

In another aspect, the invention relates to the method wherein the pentostatin and methotrexate are coadministered such that a bioactive amount of both compounds is approximately simultaneously present in a treatment site of a patient. In another aspect, the invention relates to the method wherein the pentostatin and methotrexate are coadministered such that both compounds are not approximately simultaneously bioactively present at a treatment site of a patient.

In an aspect, the invention relates to a composition comprising pentostatin and methotrexate. In another aspect, the invention relates to the composition wherein the pentostatin and methotrexate are present in an amount effective to treat rheumatoid arthritis in a host.

In another aspect, the invention relates to the method wherein the pentostatin is present in a solution comprising pentostatin in an amount of about 0.1 to about 0.3 weight percent, where the weight is based on the total compositional weight. In yet another aspect, the invention relates to the method wherein the pentostatin is present in a solution that additionally comprises mannitol and sterile water.

In an aspect, the invention relates to kits comprising pentostatin and methotrexate. In another aspect, the invention relates to the kits wherein the pentostatin and methotrexate are present in an amount effective to treat rheumatoid arthritis. In still another aspect, the invention relates to the kits wherein the pentostatin is suitable for coadministration intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically, or through local administration. In another aspect, the invention relates to the kits wherein the pentostatin is suitable for coadministration orally.

In another aspect, the invention relates to the kits wherein the methotrexate is suitable for coadministration intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically, or through local administration. In another aspect, the invention relates to the kits wherein the methotrexate is suitable for coadministration orally.

After much consideration and thought, the inventor discovered unexpectedly that coadministration of pentostatin and methotrexate may achieve surprisingly improved results over either pentostatin or methotrexate monotherapies. The implementation and background of this development will now be discussed in more detail.

In the course of further discussing the invention, however, the inventor does not wish to be bound by a particular mechanism or explanation of action, as such understanding is not necessary for the practice of the invention. Within this context, the inventor hypothesizes that the composition comprising pentostatin and methotrexate represents a successful combination therapy. This combination therapy may achieve improvement in RA at least in part through increasing the bioavailability of adenosine and deoxyadenosine. An important, and related event is the effect that coadministered pentostatin and methotrexate may have on the patient's T lymphocyte population.

First of all, adenosine, together with deoxyadenosine, is believed to play a role in inflammation. Acting at specific A2 receptors, adenosine may inhibit some, but not all, neutrophil functions. Adenosine may inhibit phagocytosis, generation of toxic oxygen metabolites, and adhesion (to some surfaces and to endothelial cells) but apparently does not inhibit degranulation or chemotaxis. Occupancy of adenosine A2 receptors seems to modulate leukocyte function by a still obscure mechanism. The presumed mechanism seems to involve occupancy of adenosine A2 receptors on neutrophils, which is believed to "uncouple" chemoattractant receptors from their stimulus-transduction proteins and inhibit function without necessarily inhibiting chemotaxis. The concentrations of adenosine that inhibit inflammatory cell function are similar to those observed in vivo and suggest a role for adenosine in the modulation of inflammation in vivo.

Pentostatin is believed to act in vivo to increase adenosine concentration by inhibiting adenosine deaminase through competitive binding. As mentioned above, such binding is biologically quite tight, with a binding coefficient of Ki of $2.5 \times 10^{-12}$M. Through this inhibition, pentostatin may slow in vivo degradation of adenosine, thus increasing its concentration and activity. Further description of the effect that pentostatin has on adenosine bioavailability and efficacy may be found in Ko, A., et al., "Clinical Response to Deoxycoformycin in Chronic Lymphoid Neoplasms and Biochemical Changes in Circulating Malignant Cells In Vivo" Blood, 72:6 1884–90 (1988); and Smyth, J. F., et al., "The Clinical Pharmacology of the Adenosine Deaminase Inhibitor 2'-Deoxycoformycin," *Cancer Chemother. Pharmacol.*, 5:93–101 (1980).

Methotrexate is believed to act in vivo by a different mechanism. While the exact mechanism is still quite uncertain, methotrexate may act through interleukin-1 release by macrophages, and monocytes. There are other proposed mechanisms as well. Recent studies have examined IL-2, IL-4, IL-10, and interferon, and found a correlation of effectiveness and modulation of cytokines from a Th1 pattern to a Th2 pattern. In a recent review, Cronstein suggested that the two mechanisms, adenosine release and cytokine alteration, play complimentary roles and that both may contribute to its effectiveness. Of course, both pentostatin and methotrexate may act to treat RA via other mechanisms than those described herein; understanding of such mechanisms is not necessary to the practice of this invention.

Next, the inventor has noted that abnormal T lymphocytes may also play a role in the development of rheumatoid arthritis. A significant number of the cells in rheumatoid synovium are activated T cells responding to a diverse range of antigens. A variety of different studies also seem to implicate T cells in the pathogenesis of rheumatoid arthritis. These include the effectiveness of thoracic duct drainage and total lymphoid irradiation in the reduction of activity of rheumatoid arthritis. Wegelius, D., et al. "Fistula of the thoracic duct as immunosuppressive therapy of rheumatoid arthritis", *Acta Med. Scand*, 187:539–544 (1970). Koczin, B. et al., "Treatment of Intractable rheumatoid arthritis with total lymphoid irradiation." *NEJM* 305:976–982 (1981). Trentham, D., et al. "Clinical and Immunologic Effects of fractionated total lymphoid irradiation in refractory rheumatoid arthritis," *New England Journal of Medicine*, 305:976–982 (1981).

One working model of T lymphocyte involvement in RA supposes that activated T cells may be controlled by inducing a (functional) adenosine deaminase (ADA) deficiency in the T cells. ADA deficiency may impact the T lymphocytes through several mechanisms. These may include: (1) the intracellular accumulation of deoxyadenosine triphosphate which is a feedback inhibitor of ribonucleotide reductase thus inhibiting DNA synthesis. Cohen, A., et al. "Deoxyadenosine triphosphate as a potentially toxic metabolite in adenosine deaminase deficiency," *Proc. Natl. Acad. Sci. USA*, 75:472–476 (1978); (2) adenosine and deoxyadenosine inhibition of S-adenosyl homocysteine hydrolase activity that prevents 1-carbon methylation reactions, Hershfield, M., "Apparent suicide inactivation of human lymphoblast S-adenosyl homocysteine hydrolase by 2'-deoxyadenosine and adenine arabinoside", *J. Biol. Chem.*, 254:22–25 (1979); and (3) depletion of nicotinamide adenine dinucleotide leading to apoptosis, Seto, S., et al. "Mechanism deoxyadenosine and 2-chlorodeoxyadenosine toxicity to nondividing human lymphocytes", *J. Clin. Invest.* 75:377–83 (1985).

T cells have been suggested to be sensitive to pharmacologic interventions particularly by methotrexate. Swanson, M., et al. "Immunosuppressive therapy: the relationship between clinical response and immunologic competence, *NEJM*, 277:163–170 (1967). In other contexts, the chemotherapeutic pentostatin also has been suggested to be effective in inhibiting T cell proliferation. Albert, D., et al., "Deoxyadenosine toxicity in hydroxyurea resistant S49 T lymphoma cells." *Exp. Cell Res.*, 179:417–428 (1988). As noted above, the combination of methotrexate and pentostatin offers the possibility of impacting the RA disease process in different ways. The inventive methods and compositions may be used with greater effectiveness than either pentostatin or methotrexate alone because their combination impacts RA in different ways. There is also the fact that the complementary pathways of these two materials may function synergistically when they are used to treat RA.

Pentostatin is a term commonly used to refer to the pharmaceutical 2'-deoxycoformycin. In the context of the invention, pentostatin also refers to pharmaceuticals that are analogs, derivatives, and prodrugs of 2'-deoxycoformycin that may be used in the practice of this invention. For example, prodrugs of 2'-deoxycoformycin may be used to increase bioavailabiity through selective bioconversion.

Pentostatin is a tight-binding inhibitor of adenosine deaminase (adenosine aminohydrolase) which has been used as a therapeutic agent for a number of disorders including hairy cell leukemia and acute lymphocytic leukemia. 2'-deoxycoformycin is available as NIPENT® (Supergen, San Ramon, Calif.).

Pentostatin has been used in the laboratory to mimic the effects of inherited adenosine deaminase deficiency which is the underlying biochemical defect in $\frac{1}{3}$ to $\frac{1}{2}$ of cases of non-X-linked severe combined immunodeficiency syndrome. Mitchell, B. et al., "Purinogenic immunodeficiency disease: Clinical features and molecular mechanisms", *Ann Int. Med.* 92:826–831m (1980).

The clinical use of pentostatin has primarily been with T lymphocyte malignancies including T-cell acute lymphocytic leukemia, lymphocytic lymphoma, chronic lymphocytic leukemia and mycosis fungoides (Sezary Syndrome). Pentostatin, in doses of 1.0 to 13.5 mg/kg results in cytoreduction but no clinically meaningful remission in CLL. Toxicity at very high doses is substantial and may include renal failure secondary to acute tubular necrosis, central nervous system toxicity (seizures), pulmonary edema, and keratoconjunctivitis. Koller, C., et al., "Alterations in erythrocyte adenine nucleotide pools resulting from 2'-deoxycoformycin therapy", *Cancer Research*, 43:1409–1414, 1983. Toxicity at lower doses, e.g. 5 mg/M$^2$ on two successive days, may be mild with transient leukopenia, nausea and lethargy or somnolence. Even lower doses (4 mg/M$^2$ once a week×3 or 4 followed by once every three to four weeks) produced no toxicity yet were effective in inducing remission in hairy cell leukemia. Johnston, J., et al., "The treatment of hairy-cell leukemia with 2'-deoxycoformycin), *British Jour. of Haem.* 63:525–534 (1989).

Methotrexate is a term commonly used to refer to the pharmaceutical N-[4-[[(2,4-diamino-6-pteridinyl)methyl] methylamino]benzoyl]-L-glutamic acid. In the context of the invention, methotrexate also refers to pharmaceuticals that are analogs, derivatives, and prodrugs of N-[4-[[(2,4-diamino-6-pteridinyl)methyl]methylamino]benzoyl]-L-glutamic acid that may be used in the practice of this invention. For example, prodrugs of N-[4-[[(2,4-diamino-6-pteridinyl)methyl]methylamino]benzoyl]-L-glutamic acid may be used to increase bioavailability through selective bioconversion. N-[4-[[(2,4-diamino-6-pteridinyl)methyl] methylamino]benzoyl]-L-glutamic acid may be obtained in an oral dosage form as RHEUMATREX® from the Immunex Corporation.

Methotrexate is used in RA therapy preferably when the disease is characterized as severe, active, classical, or definite RA (but not less severe disease) because of the possibility of severe drug side effects, including irritation of the mouth (stomatitis), irritation of the intestines resulting in diarrhea, irritation of the lung on rare occasions (pneumonitis), rash and the possibility of liver damage. The issue of liver toxicity is still controversial, but the risk appears to be quite small. The American College of Rheumatology has issued guidelines to monitor for hepatoxicity. These guidelines include measuring liver enzymes, serum albumin and excluding patients at risk for alcoholic liver disease as well as diabetics, morbidly obese individuals and others at risk for fatty liver. Elderly patients and those with diminished kidney function can get lowered blood counts. To some extent, this is due to interference with folic acid (a vitamin) metabolism, and can be obviated by supplemental folic acid (1 mg. per day).

Patients who are good candidates for being treated according to the invention are those that have relatively severe RA. This is because the inventive methods and compositions comprise potent pharmaceuticals that may cause significant side effects. This makes them an undesirable choice for therapy if the RA is not relatively severe, and where less potent pharmaceuticals are effective. Relatively severe RA may be considered Stage II or III RA as defined by the 1987 ARA revised criteria, with multiple (6 or more) swollen joints, and at least two of the following: morning stiffness lasting more than 30 minutes, greater than or equal to 20 mm/h erythrocyte sedimentation rate (ESR), elevated C reactive protein (CRP) $\geq 6$.

In fact, it is to be expected that patients receiving the inventive composition may have been on a stable dose of prednisone ($\leq 10$ mg/day), and a non-steroidal anti-inflammatory drug (NSAID) at recommended doses for a period of time before being treated using the inventive method, although this is not necessary to practice the invention. Additionally, patients may, if their physician deems it necessary, continue these medications at their entry doses for the duration of their treatment according to the invention.

The amounts of methotrexate and pentostatin that are coadministered during the practice of this invention will vary from patient to patient. Coadministration in the context of this invention is defined to mean the administration of more than one therapeutic in the course of a coordinated treatment to achieve an improved clinical outcome. Such coadministration may also be coextensive, that is, occurring during overlapping periods of time.

Methotrexate may be coadministered in an amount that demonstrates a beneficial effect, but does not cause untoward side effects, as determined by the patient s physician. Similarly, pentostatin may be coadministered in an amount that demonstrates a beneficial effect, but does not cause untoward side effects, as determined by the patient's physician. In a preferable embodiment, the dose of methotrexate is approximately equal to or less than 15 mg/week. In another preferable embodiment, the dose of pentostatin is approximately equal to or less than 10 mg/m$^2$ monthly. In a more preferable embodiment, patients may be coadministered 2 mg/m$^2$ pentostatin monthly and up to 15 mg per week of methotrexate. In another preferable embodiment, pentostatin is coadministered in an amount up to about 4-mg/m$^2$ monthly. More preferably, pentostatin is coadministered in an amount up to about 4-mg/m$^2$ monthly with up to about 15 mg. of methotrexate per week.

Pentostatin and methotrexate may be coadministered in any number of typical dosage forms. For example, either or both of pentostatin may be administered intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically or through local administration. Such administration would be according to procedures well understood in the art.

In a preferable embodiment, pentostatin is coadministered intravenously in 50 cc. 0.9 Normal Saline (NS) over a 30 minute period, together with intravenous hydration of 500 cc of 0.9 NS over 1 hour before and after pentostatin. In a preferable embodiment, a pentostatin containing solution includes pentostatin in an amount of about 0.02 to about 1 weight percent, more preferably about 0.1 to about 0.3 weight percent, where the weight is based on the total compositional weight. Furthermore, the composition may contain additional ingredients, such as conventional pharmaceutical excipients. In a preferable embodiment, the composition additionally comprises mannitol, and sterile water. Sodium hydroxide or hydrochloric acid may also be added to adjust pH. In another preferable embodiment, methotrexate is administered orally using a tablet containing about 2.5 mg equivalent of methotrexate.

Additionally, it is possible to coadminister pentostatin and methotrexate as a single composition, rather than as separate compositions. For example, pentostatin and methotrexate may be coadministered intravenously using a solution containing both pharmaceuticals.

Next, in another embodiment of the invention, methotrexate is coadministered over an period approximately coextensive with pentostatin, but in a separate dosage form. For example, in a preferable embodiment, methotrexate may be administered orally while pentostatin is administered intravenously and approximately coextensively. In another embodiment, methotrexate is coadministered over an approximately coextensive period, but in a similar or the same dosage form, as pentostatin. In yet another embodiment, both methotrexate and pentostatin are coadministered orally. Additionally, pentostatin and methotrexate may be coadministered such that a bioactive amount of both compounds is approximately simultaneously present in a treatment site of a patient. Alternatively, pentostatin and methotrexate may be coadministered such that both compounds are not approximately simultaneously bioactively present in a treatment site of a patient. For example. methotrexate may be coadministered, and then, after the methotrexate is no longer bioavailable, the pentostatin may be administered.

Deoxycoformycin as an inhibitor of adenosine deaminase can be synergized in T lymphocyte toxicity by the administration of deoxyadenosine. In another, preferable, embodiment, pentostatin and methotrexate may be coadministered with deoxyadenosine.

Kits containing pentostatin and methotrexate are also within the scope of the invention. These kits may contain pentostatin and methotrexate such that the pharmaceuticals are stored apart from one another. Additionally, the kits may contain the pharmaceuticals in a composition, as discussed above, that comprises both pentostatin and methotrexate. Furthermore, the amounts and dosage forms of pentostatin and methotrexate may be varied, according to the previous discussion.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

Various embodiments of the invention are described in the following examples.

EXAMPLES

Example 1

Deoxycoformycin was administered (1 or 2 mg/m$^2$ intravenously monthly) to eight patients with active rheumatoid arthritis who were receiving methotrexate (less than or equal to 15 mg/wk) in an open label study.

Patients were evaluated for swelling and tenderness using standard joint counts and pain on a 10 cm visual analogue scale during 15 visits over a six month period. Surrogate markers measured via laboratory analysis included erythrocyte sedimentation rate (ESR), C reactive protein (CRP), and rheumatoid factor.

Comparing early to late time points (average of first three visits to average of last three visits), four of eight patients had improved swelling and tenderness. Two of the eight patients had reduced pain scores. Laboratory studies demonstrated that three of four patients with elevated baseline ESR's improved. Two of the eight patients had a decline in their rheumatoid factor and one of the eight patients had a decline in CRP. Transient nausea, controlled by antiemetic medication, was the only side effect.

Using either American College of Rheumatology or Paulus criteria, the results of this experiment demonstrate that the combination therapy is an effective treatment for rheumatoid arthritis.

Example 2

Deoxycoformycin is administered (4 mg/m$^2$ intravenously monthly) to a sample set of patients with active rheumatoid arthritis who are receiving methotrexate (less than or equal to 15 mg/wk) in an open label study.

Patients are evaluated for swelling and tenderness using standard joint counts and pain on a 10 cm visual analogue scale during 15 visits over a six month period. Surrogate markers measured via laboratory analysis include erythrocyte sedimentation rate (ESR), C reactive protein (CRP), and rheumatoid factor.

Early to late time points (average of first three visits to average of last three visits), are compared with regard to swelling and tenderness; pain scores; ESR, CRP and rheumatoid factor. Transient nausea, if present, is controlled by antiemetic medication.

Either American College of Rheumatology or Paulus criteria, or both, are used to determine if the combination therapy is an effective treatment for rheumatoid arthritis.

What is claimed is:

1. A method of treating a patient having rheumatoid arthritis comprising administering to the patient a therapeutically effective amount of pentostatin in combination with a therapeutically effective amount of methotrexate, such that the efficacy of the therapy is enhanced through synergistic effects of pentostatin and methotrexate.

2. The method of claim 1, wherein the pentostatin is coadministered intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically, or through local administration.

3. The method of claim 2, wherein the pentostatin is coadministered intraarticularly.

4. The method of claim 2, wherein the pentostatin is coadministered intravenously.

5. The method of claim 1, wherein the pentostatin is coadministered in an amount up to about 4 mg/m$^2$ monthly.

6. The method of claim 1, wherein the methotrexate is coadministered intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically or through local administration.

7. The method of claim 6, wherein the methotrexate is coadministered orally.

8. The method of claim 7, wherein the methotrexate is coadministered orally in the form of a tablet containing about 2.5 mg equivalent of methotrexate.

9. The method of claim 1, wherein the methotrexate and pentostatin are coadministered coextensively.

10. The method of claim 1, wherein the methotrexate and pentostatin are not coadministered coextensively.

11. The method of claim 1, wherein the methotrexate is coadministered over an period approximately coextensive with the pentostatin, but in a separate dosage form.

12. The method of claim 1, wherein the methotrexate is coadministered over an approximately coextensive period, but in a similar or the same dosage form, as the pentostatin.

13. The method of claim 1, wherein both methotrexate and pentostatin are coadministered orally.

14. The method of claim 1, wherein the pentostatin and methotrexate are coadministered such that a bioactive amount of both compounds is approximately simultaneously present in a treatment site of a patient.

15. The method of claim 1, wherein the pentostatin and methotrexate are coadministered such that both compounds are not approximately simultaneously bioactively present at a treatment site of a patient.

16. A composition comprising pentostatin and methotrexate in an amount that is therapeutically synergistic and effective to treat rheumatoid arthritis in a host.

17. The composition of claim 16, wherein pentostatin is present in a solution comprising pentostatin in an amount of about 0.1 to about 0.3 weight percent, where the weight is based on the total compositional weight.

18. The composition of claim 16, wherein the pentostatin is present in a solution that additionally comprises mannitol and sterile water.

19. A kit comprising pentostatin and methotrexate each in an amount that is therapeutically synergistic and effective to treat rheumatoid arthritis in a host.

20. The kit of claim 19, wherein the pentostatin is suitable for coadministration intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically, or through local administration.

21. The kit of claim 19, wherein the pentostatin is suitable for coadministration orally.

22. The kit of claim 19, wherein the methotrexate is suitable for coadministration intravenously, intramuscularly, orally, by inhalation, parenterally, intraperitoneally, intraarterially, transdermally, sublingually, nasally, through use of suppositories, transbuccally, liposomally, adiposally, intraocularly, subcutaneously, intraarticularly, intrathecally, topically, or through local administration.

23. The kit of claim 19, wherein the methotrexate is suitable for coadministration orally.

\* \* \* \* \*